United States Patent [19]
Oh-Kita et al.

[11] Patent Number: 4,891,347
[45] Date of Patent: Jan. 2, 1990

[54] PROCESS FOR THE PREPARATION OF CATALYST USED IN THE PRODUCTION OF UNSATURATED CARBOXYLIC ACIDS

[75] Inventors: Motomu Oh-Kita; Kazuhiro Ishii; Masaaki Kato; Masao Kobayashi, all of Otake, Japan

[73] Assignee: Mitsubishi Rayon Co., Ltd., Tokyo, Japan

[21] Appl. No.: 795,820

[22] Filed: Nov. 7, 1985

[30] Foreign Application Priority Data

Nov. 8, 1984 [JP] Japan .................................. 59-234140

[51] Int. Cl.$^4$ .................... B01J 27/185; B01J 27/188; B01J 27/19; B01J 27/198
[52] U.S. Cl. .................................... 502/206; 502/209; 502/211; 562/532; 562/535
[58] Field of Search ..................... 502/206, 209, 211

[56] References Cited

U.S. PATENT DOCUMENTS

| 4,049,575 | 9/1977 | Sasaki et al. ..................... 502/209 X |
| 4,066,704 | 1/1978 | Harris et al. ..................... 502/211 X |
| 4,184,981 | 1/1980 | Vanderspurt ......................... 502/209 |
| 4,268,448 | 5/1981 | Franz et al. ...................... 502/209 X |
| 4,335,018 | 6/1982 | Franz et al. ...................... 502/211 X |
| 4,447,558 | 5/1984 | Sasaki et al. ..................... 502/211 X |
| 4,469,810 | 9/1984 | Kato et al. ....................... 502/211 X |
| 4,489,170 | 12/1984 | Krabetz et al. ................... 502/211 X |
| 4,558,029 | 12/1985 | Paparizos ......................... 502/209 X |

FOREIGN PATENT DOCUMENTS 0109259  5/1984  European Pat. Off. ............ 502/353

OTHER PUBLICATIONS

Surface, 24(6) 1986.
Readings of the 7th International Congress on Catalysis, Part B 1047-1056.

Primary Examiner—W. J. Shine
Attorney, Agent, or Firm—Armstrong, Nikaido, Marmelstein & Kubovcik

[57] ABSTRACT

The present invention provides a process for the preparation of a catalyst used in the production of unsaturated carboxylic acids such as methacrylic acid by the gas phase catalytic oxidation of the corresponding unsaturated aldehydes such as methacrolein. Said catalyst is composed of a multi-component composition containing at least phosphorus, molybdenum and antimony. The present invention has attained an improved in its catalytic performance such as conversion rate, selectivity, single-pass yield etc. by using antimony trioxide with average particle size of no more than 0.2 micron as a starting material upon preparing said catalyst.

4 Claims, No Drawings

PROCESS FOR THE PREPARATION OF CATALYST USED IN THE PRODUCTION OF UNSATURATED CARBOXYLIC ACIDS

FIELD OF THE INVENTION

This invention relates to a process for the preparation of a catalyst used in the production of unsaturated carboxylic acids by the gas phase catalytic oxidation of the corresponding unsaturated aldehydes.

DESCRIPTION OF THE PRIOR ART

Numerous processes have been proposed which utilize catalysts containing phosphorus, molybdenum, and antimony in the production of unsaturated carboxylic acids by the gas phase catalytic oxidation of the corresponding aldehydes. Examples include Japanese Patent Publication [Kokoku] No. 13702/81 (catalyst composition: P, Mo, Sb, Cu), Publication [Kokoku] No. 48497/81 [P, Mo, V, Sb (Fe, Ni, Mg, Ca, Al, W, Cu, Pb, Cr)], and U.S. Pat. No. 4,240,930 (P, Mo, Cu, Sb, Cs). However, these are not always adequate as industrial catalysts as they all have major drawbacks, such as poor reaction yields, rapid loss of catalytic activity with time, and excessively high reaction temperature.

SUMMARY OF THE INVENTION

Upon conducting extensive research aimed at improving existing methods of catalyst preparation, we discovered a novel process for the preparation of an excellent catalyst that is effective at lower reaction temperatures than catalysts prepared by prior art methods, and which gives high yields of unsaturated carboxylic acids.

DETAILED DESCRIPTION OF THE INVENTION

According to the present invention, in a process for preparing a catalyst for the production of unsaturated carboxylic acids, the catalyst being a multi-component catalyst containing at least phosphorus, molybdenum, and antimony in the catalyst composition, there is provided the improvement which comprises making use of antimony trioxide having an average particle size of not more than 0.2 micron as a starting material.

Use of the catalyst obtained by the process disclosed here makes possible the advantageous production of unsaturated carboxylic acids from the corresponding unsaturated aldehydes, and in particular acrylic acid or methacrylic acid from acrolein or methacrolein.

The atomic ratios of the phosphorus, antimony, and other elements present in the catalyst obtained by the present process should preferably lie within the following ranges, based on a value of 12 for the molybdenum: phosphorus, 0.3 to 3; antimony, 0.05 to 3, alkali metals and thallium combined, 0 to 3; all other components combined, 0 to 10. Potassium, rubidium, and cesium are especially favorable as the alkali metals. Other elements that may serve as components of the catalyst include vanadium, silver, magnesium, zinc, selenium, tellurium, arsenic, copper, germanium, nickel, silicon, rhodium, tungsten, boron, tantalum, chromium, barium, tin, iron, and the like.

In the present invention, antimony trioxide having an average particle size of not more that 0.2 micron must be used as the starting material. If the starting material has an average particle size larger than this, catalyst with a superior performance cannot be obtained. The preferable range in the average particle size is 0.1 to 0.01 micron. The average particle sizes given here are the values obtained by measurement using an electron microscopy or a BET adsorption method. The average particle size of most commercially available industrial antimony trioxide ranges from 0.5 to 7 micron. This may be used after pulverizing to an average particle size of not more that 0.2 micron. Various methods exist for reducing coarser antimony trioxide to the desired particle size, examples of which include the classification of commercially available powder using a sieve of the required pore size, and an evaporation process in which antimony metal is evaporated to fine particles with an electrical arc and simultaneously converted into the trioxide.

Nitrates, ammonium salts, halides, oxides, and the like compounds of the various elements may be employed as the starting materials used for preparing the catalyst.

When working the invention, starting materials for the catalyst excluding the antimony trioxide is first dissolved or dispersed in water. The antimony trioxide may be added after this starting material mixture has been heated and the water driven off, but it is preferable to first add antimony trioxide to the mixture and stir thoroughly, then heat and drive off the water. The desired catalyst may be obtained by heat treatment, under a stream of air, of the solid thus obtained.

The catalyst prepared by means of the present process may be supported on inert carriers such as silica, alumina, silica/alumina, and silicon carbide, or used after dilution with any of these materials.

The catalyst of the invention is generally used in a fixed bed, but may be used also in a fluidized bed. The concentration of unsaturated aldehyde in the feedstock gas may be varied over a wide range, but a concentration of from 1 to 20% by volume, and particularly 3 to 10% by volume is preferable. Although using ordinary air as the oxygen source is economical, air enriched with pure oxygen may also be used. The oxygen concentration within the feedstock gas is represented as the molar ratio with respect to unsaturated aldehyde, a value of which should preferably range from 0.3 to 4, and especially 0.4 to 2.5. The feedstock gas may be diluted by the addition of inert gases such as nitrogen, steam, carbon dioxide, and the like. The reaction pressure should range from atmospheric pressure to several atmospheres, and the reaction temperature should be from 240° to 450° C., and preferably from 260° to 400° C.

The conversion (%) of unsaturated aldehyde, and the selectivity (%) for and single-pass yield (%) of the unsaturated carboxylic acid formed, which are used in the following examples are defined below:

$$\text{Conversion (\%) of unsaturated aldehyde} = \frac{\text{moles of unsaturated aldehyde that reacted}}{\text{moles of unsaturated aldehyde fed}} \times 100$$

$$\text{Selectivity (\%) for unsaturated carboxylic acid} = \frac{\text{moles of unsaturated carboxylic acid produced}}{\text{moles of unsaturated aldehyde that reacted}} \times 100$$

$$\text{Single-pass yield (\%) of unsaturated carboxylic acid} = \frac{\text{moles of unsaturated carboxylic acid produced}}{\text{moles of unsaturated aldehyde fed}} \times 100$$

EXAMPLE 1

One hundred parts of ammonium paramolybdate was dissolved in 400 parts of pure water. To this was added, under stirring, a solution of 6.5 parts of 85% phosphoric acid dissolved in 50 parts pure water. This was followed by the addition, also under stirring, of 4.1 parts of antimony trioxide with an average particle size of 0.03 micron, subsequent to which the solution mixture was heated and evaporated to dryness. After being dried at 130° C., this solid was pulverized and compression molded, then heat-treated at 380° C. under a stream of air for five hours. The composition of the catalyst obtained, excluding oxygen (likewise hereunder), was $P_{1.2}Mo_{12}Sb_{0.5}$. This catalyst was packed into a reactor and a mixed gas consisting of methacrolein (5% by volume), oxygen (10%), steam (30%), and nitrogen (55%) was passed through for a contact period of 3.6 seconds at a reaction temperature of 310° C. The product was collected and analyzed by gas chromatography. Methacrolein conversion was 52.5%, selectivity for methacrylic acid was 66.0%, and the methacrylic acid single-pass yield was 34.7%.

COMPARATIVE EXAMPLE 1

A catalyst of the same composition as in Example 1 was prepared in the same manner, except that antimony trioxide with an average particle size of 3 microns was used. When this catalyst was used to carry out a reaction under identical conditions as in Example 1, methacrolein conversion was 47.3%, selectivity for methacrylic acid was 63.8%, and the single-pass yield of methacrylic acid was 30.2%.

EXAMPLE 2

One hundred parts of ammonium paramolybdate, 2.8 parts of ammonium metavanadate, and 4.8 parts of potassium nitrate were dissolved in 400 parts of pure water. To this were added a solution of 8.2 parts of 85% phosphoric acid dissolved in 50 parts pure water and a solution of 2.5 parts of germanium dioxide dissolved in 50 parts pure water. This was followed by the addition of 5.5 parts antimony trioxide having an average particle size of 0.02 micron, and the mixture heated at 60° C. and stirred. Next, a solution of 5.7 parts of cupric nitrate dissolved in 50 parts pure water was added, and the mixture evaporated to dryness under heating. After drying the resulting solid at 130° C., then pulverizing and compression molding, the catalyst was heat treated for five hours at 380° C. under a stream of air. The composition of the catalyst obtained was $P_{1.5}Mo_{12}V_{0.5}Cu_{0.5}Ge_{0.5}K_1Sb_{0.8}$. This catalyst was packed into a reactor and a reaction carried out under the same conditions as in Example 1, except that the reaction temperature was set at 300° C. Methacrolein conversion was 81.5%, selectivity for methacrylic acid 86.4%, and the singlepass yield of methacrylic acid 70.4%.

COMPARATIVE EXAMPLE 2

A catalyst having the same composition as in Example 2 was prepared in an identical manner, save for the use of antimony trioxide with an average particle size of 2 microns. When a reaction was conducted using this catalyst under the same reaction conditions as in Example 2, methacrolein conversion was 79.8%, selectivity for methacrylic acid was 85.6%, and the single-pass yield of methacrylic acid was 68.3%.

EXAMPLE 3

Catalyst was prepared in the same way as in Example 2 using antimony trioxide with an average particle size of 0.03 micron. The composition of this catalyst was $P_{1.6}Mo_{12}V_{0.8}Cu_{0.2}Se_{0.2}Ag_{0.1}Ba_{0.1}Rb_1Sb_{0.5}$. Using this catalyst, a reaction was conducted under the same reaction conditions as in Example 1 at a reaction temperature of 290° C. The results are given in the table below.

COMPARATIVE EXAMPLE 3

A catalyst having the same composition as in Example 3 was prepared in an identical manner, save for the use of antimony trioxide with an average particle size of 2 microns. This catalyst was used in a reaction conducted under the same conditions as in Example 1 at a reaction temperature of 290° C. The results are given in the table below.

EXAMPLE 4

Catalyst was prepared in the same way as Example 2 using antimony trioxide with an average particle size of 0.1 micron. The composition of the resulting catalyst was $P_1Mo_{12}Rh_{0.01}Cr_{0.5}Tl_2Zn_2Sb_2Ta_{0.5}$. Using this catalyst, a reaction was conducted under the same reaction conditions as in Example 1 at a reaction temperature of 275° C. The results are given in the table below.

COMPARATIVE EXAMPLE 4

A catalyst having the same composition as in Example 4 was prepared in an identical manner, save for the use of antimony trioxide with an average particle size of 0.07 micron. This catalyst was used in a reaction conducted under the same conditions as in Example 1 at a reaction temperature of 275° C. The results are given in the table below.

EXAMPLE 5

A catalyst was prepared in the same way as Example 2 using antimony trioxide with an average particle size of 0.05 micron. The composition of the resulting catalyst was $P_2Mo_{12}W_{0.2}Fe_{0.5}B_{0.2}Ni_{0.5}Cs_2Sb_1$. Using this catalyst, a reaction was conducted under the same reaction conditions as in Example 1 at a reaction temperature of 340° C. The results are given in the table below.

COMPARATIVE EXAMPLE 5

A catalyst having the same composition as in Example 5 was prepared using antimony trioxide with an average particle size of 4 microns. This catalyst was used in a reaction conducted under the same conditions as in Example 1 at a reaction temperature of 340° C. The results are given in the table below.

EXAMPLE 6

A catalyst was prepared in the same way as Example 2 using antimony trioxide with an average particle size of 0.08 micron. The composition of the resulting catalyst was $P_1Mo_{12}V_{0.6}As_{0.1}Cu_{0.1}Sn_1Rb_1Sb_{0.1}$. Using this catalyst, a reaction was conducted under the same reaction conditions as in Example 1 at a reaction temperature of 300° C. The results are given in the table below.

COMPARATIVE EXAMPLE 6

A catalyst having the same composition as in Example 6 was prepared using antimony trioxide with an average particle size of 3 microns. This catalyst was used in a reaction conducted under the same conditions as in Example 1 at a reaction temperature of 300° C. The results are given in the table below.

EXAMPLE 7

A catalyst was prepared in the same way as Example 2 using antimony trioxide with an average particle size of 0.03 micron. The composition of the resulting catalyst was $P_1Mo_{12}V_{0.5}Mg_1Te_{0.6}Si_{0.2}K_{0.8}Cs_{0.3}Sb_{0.7}$. Using this catalyst, a reaction was conducted under the same reaction conditions as in Example 1 at a reaction temperature of 295° C. The results are given in the table below.

COMPARATIVE EXAMPLE 7

A catalyst having the same composition as in Example 7 was prepared using antimony trioxide with an average particle size of 3 microns. This catalyst was used in a reaction conducted under the same conditions as in Example 1 at a reaction temperature of 295° C. The results are given in the table below.

90.5%, a selectivity for acrylic acid of 89.0%, and a single-pass yield of acrylic acid of 80.5%.

We claim:

1. In a process for the preparation of catalyst for use in the production of unsaturated carboxylic acids, said catalyst having a multi-component composition comprising phosphorus, molybdenum, and antimony, wherein the method for producing said catalyst comprises first dissolving or dispersing the catalytic components in water, except for antimony trioxide, subsequently adding antimony trioxide and driving off the water either before or after the antimony trioxide is added, and then heat treating said catalytic components containing antimony trioxide in the presence of oxygen, the improvement comprising using antimony trioxide having an average particle size of not more than 0.2 micron as a starting material.

2. The process according to claim 1 wherein the average particle size of antimony is from 0.1 to 0.01 micron.

3. A catalyst obtained by the process according to claim 1, where the atomic ratio of the catalyst compo-

TABLE

|  | Average particle size of antimony trioxide (μ) | Reaction temperature (°C.) | Conversion of methacrolein (%) | Selectivity for methacrylic acid (%) | Single-pass yield of methacrylic acid (%) |
|---|---|---|---|---|---|
| Example 3 | 0.03 | 290 | 84.0 | 89.0 | 74.8 |
| Comparative Example 3 | 2 | 290 | 82.5 | 88.6 | 73.1 |
| Example 4 | 0.1 | 275 | 83.3 | 84.1 | 70.1 |
| Comparative Example 4 | 0.7 | 275 | 81.0 | 83.2 | 67.4 |
| Example 5 | 0.05 | 340 | 80.1 | 84.9 | 68.0 |
| Comparative Example 5 | 4 | 340 | 76.5 | 83.4 | 63.8 |
| Example 6 | 0.08 | 300 | 83.2 | 86.8 | 72.2 |
| Comparative Example 6 | 3 | 300 | 81.0 | 86.1 | 69.7 |
| Example 7 | 0.03 | 295 | 85.4 | 83.6 | 71.4 |
| Comparative Example 7 | 3 | 295 | 83.3 | 82.5 | 68.7 |

EXAMPLE 8

Using the catalyst prepared in Example 2, a gas mixture consisting of acrolein (5% by volume), oxygen (10%), steam (30%), and nitrogen (55%) was introduced into a catalyst layer for a contact time of 3.6 seconds at a reaction temperature of 290° C. The results were an acrolein conversion of 91.8%, a selectivity for acrylic acid of 90.3%, and a single-pass yield of acrylic acid of 82.9%.

COMPARATIVE EXAMPLE 8

A reaction was conducted using the catalyst in Comparative Example 2 under the same reaction conditions as in Example 8, giving an acrolein conversion of nents, based on a value of 12 for molybdenum, is 0.3 to 3 for phosphorus, 0.05 to 3 for antimony, and further comprising alkali metals and thallium in an atomic ratio of from 0 to 3, and an atomic ratio of from 0 to 10 for all other components.

4. The process for the preparation of catalyst for use in the production of unsaturated carboxylic acids of claim 1, wherein the catalyst having a multi-component composition consists essentially of PMoSbXY, wherein X represents V, Ag, Mg, Zn, Se, Te, As, Cu, Ge, Ni, Si, Rh, W, B, Ta, Cr, Ba, Sn, and Fe, and Y represents a metal selected from the group consisting of potassium, rubidium, cesium and thallium.

* * * * *